United States Patent
Royall et al.

(10) Patent No.: US 10,634,687 B2
(45) Date of Patent: Apr. 28, 2020

(54) SERUM BIOMARKER SCREEN FOR THE DIAGNOSIS OF CLINICAL AND PRECLINICAL ALZHEIMER'S DISEASE

(71) Applicants: Donald R. Royall, San Antonio, TX (US); Raymond F. Palmer, San Antonio, TX (US)

(72) Inventors: Donald R. Royall, San Antonio, TX (US); Raymond F. Palmer, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 13/943,654

(22) Filed: Jul. 16, 2013

(65) Prior Publication Data
US 2014/0018446 A1    Jan. 16, 2014

Related U.S. Application Data

(60) Provisional application No. 61/671,858, filed on Jul. 16, 2012.

(51) Int. Cl.
*G01N 33/53* (2006.01)
*G01N 33/542* (2006.01)
*A61K 38/00* (2006.01)
*G01N 33/68* (2006.01)

(52) U.S. Cl.
CPC ..... *G01N 33/6896* (2013.01); *G01N 2800/60* (2013.01)

(58) Field of Classification Search
None
See application file for complete search history.

(56) References Cited

U.S. PATENT DOCUMENTS

2013/0224117 A1    8/2013    Royall et al.

OTHER PUBLICATIONS

Finnery et al., J. Burn Care and Res., 2011, 32, Suppl 2, pp. S51.*
Baldo et al., Verbal and design fluency in patients with frontal lobe lesions. J. Int. Neurosci. 7, 586-596 (2001).
Barberger-Gateau et al., Instrumental Activities of Daily Living as a Screening Tool for Cognitive Impairment and Dementia in Elderly Community Dwellers. J. Am. Geriatr. Soc. 40, 1129-1134 (1992).
Bennett et al. Cognitive, extrapyramidal, and magnetic resonance imaging predictors of functional impairment in nondemented older community dwellers: the Sydney older person study. J. Am. Geriatr. Soc. 54, 3-10 (2006).
Bentler, P. M., Comparative Fit Indexes in Structural Models. Psychol. Bull. 107, 238-246 (1990).
Bouchard, T. J., Genetic influence on human intelligence (Spearman's 'g'): How much? Ann. Hum. Biol. 36, 527-544 (2009).
Browne, M. W., Cudeck, R. Alternative ways of assessing model fit, in Bollen, K.A., Long, J.S. (Eds.), Testing structural equation models, Sage Publications, Thousand Oaks, CA, pp. 136-162 (1993).
Burton et al., Functional abilities in older adults with mild cognitive impairment. Gerontol. 55, 570-581 (2009).
Choi et al., Multiple bases of human intelligence revealed by cortical thickness and neural activation. J. Neuroscience 28(41), 10323-10329 (2008).
Chui et al., Criteria for the diagnosis of ischemic vascular dementia proposed by the State of California Alzheimer's Diagnostic and Treatment Centers. Neurol. 42, 473-480 (1992).
Duncan et al., Common regions of the human frontal lobe recruited by diverse cognitive demands. Cogn. Neuropsychol. 14, 713-741 (1997).
Duncan et al., A neural basis for general intelligence. Science 289, 457-460 (2000).
Folstein et al., "Mini-Mental State": A practical method for grading the cognitive state of patients for the clinician. J. Psychiatr. Res. 12, 189-198 (1975).
Gläscher et al., Distributed neural system for general intelligence revealed by lesion mapping. PNAS 107, 4705-4709 (2010).
Goldberg et al., Performance-based measures of everyday function in mild cognitive impairment. Am J Psychiatry 167, 845-853 (2010).
Gottfredson, L. Why g matters: The complexity of everyday life. Intelligence 24, 79-132 (1997).
Grabowski, T. J., Damasio, A. R. Definition, clinical features and neuroanatomica basis of dementia. In the Neuropathology of Dementia, Eisiri MM, Morris JH (eds). Cambridge University Press: Cambridge. (1997).
Graham, J. W., Missing Data Analysis: Making it Work in the Real World. An. Rev. Psychol. 6, 549-576 (2009).
Grundman et al., Mild cognitive impairment can be distinguished from Alzheimer Disease and normal aging for clinical trials. Arch. Neurol. 61, 59-66 (2004).
Hughes et al., New clinical scale for the staging of dementia. Br. J. Psychiatry 140, 566-572 (1982).
Jefferson et al. Characterization of activities of daily living in individuals with mild cognitive impairment. Am. J. Geriatr. Psychiatry 16, 375-383 (2008).
Lawton, M. P., Brody, E. M. Assessment of older people: self-maintaining and instrumental activities of daily living. Gerontologist 9, 179-186 (1969).
Luck et al., Impact of impairment in instrumental activities of daily living and mild cognitive impairment on time to incident dementia: results of the Leipzig Longitudinal Study of the Aged. Psychol. Med. 41, 1087-1097 (2011).

(Continued)

*Primary Examiner* — Olga N Chernyshev
(74) *Attorney, Agent, or Firm* — Norton Rose Fulbright US LLP (57) ABSTRACT

Certain embodiments are directed to methods of identifying dementia in subjects comprising, measuring serum levels of one or more of interferon gamma, IL-10, IL-12p40, IL-13, alpha 2 macroglobulin, beta 2 microglobulin, pancreatic polypeptide, prolactin, stem cell factor, thrombopoietin, and Von Willebrand Factor and identifying a subject as having dementia if the levels of the biomarkers is increased.

1 Claim, 6 Drawing Sheets

(56) References Cited

OTHER PUBLICATIONS

O'Bryant et al., Staging dementia using clinical dementia rating scale sum of boxes scores: A Texas Alzheimer's Research Consortium study. Arch. Neurol. 65, 1091-10 (2008).
O'Bryant et al. A Serum Protein-Based Algorithm for the Detection of Alzheimer's Disease. 67(9), 1077-1081 (2010).
O'Bryant et al. A blood-based algorithm for the detection of Alzheimer's disease. Dement. Geriatr. Cogn. Disord. 32(1), 55-62 (2011a).
O'Bryant et al. A Blood-Based Screening Tool for Alzheimer's Disease That Spans Serum and Plasma: Findings from TARC and ADNI, PLoS ONE 6(12), e28092 (2011b).
Perneczky et al. Complex activities of daily living in mild cognitive impairment: conceptual and diagnostic issues. Age Ageing. 35, 240-245 (2006).
Ravetti, G. M., Moscato, P. Identification of a 5-Protein Biomarker Molecular Signature for Predicting Alzheimer's Disease. 3(9), E3111 (1-12), (2008).
Royall et al. The cognitive correlates of functional status: A review from the Committee on Research of the American Neuropsychiatric Association. J Neuropsychiatry Clin Neurosci 19, 249-265 (2007).
Royall, D. R., Palmer, R. F. Getting Past "g": Testing a new model of dementing processes in non-demented persons. Journal of Neuropsychiatry and Clinical Neurosciences 24:37-46 (2012).
Salthouse, T. A., Relations between cognitive abilities and measures of executive functioning. Neuropsychol. 19, 532-545 (2005).
Schafer, J. L., Graham, J. W. Missing Data: Our View of the State of the Art. Psychol. Methods, 7, 147-177 (2002).
Spearman, C. "General Intelligence," Objectively determined and measured. Am. J. Psychol. 15, 201-293. (1904).
Tombaugh, T. N., McIntyre, N. J. The Mini-Mental State Examination: A Comprehensive Review. J. Am. Geriatrics Soc 40, 922-935 (1992).
Winblad et al. Mild cognitive impairment—beyond controversies, towards a consensus: report of the International Working Group on Mild Cognitive Impairment J. Intern. Med. 256, 240-246 (2004).
Zweig, M. H., Campbell, G. Receiver-operating characteristic (ROC) plots: a fundamental evaluation tool in clinical medicine. Clin. Chem. 39, 561-577 (1993).

\* cited by examiner

SERUM BIOMARKER SCREEN FOR THE DIAGNOSIS OF CLINICAL AND PRECLINICAL ALZHEIMER'S DISEASE

PRIORITY CLAIM

This application claims priority to U.S. Provisional Application 61/671,858 filed Jul. 16, 2012, which is incorporated herein by reference in its entirety.

BACKGROUND

Currently, the clinical diagnosis of Alzheimer's disease (AD) and/or mild cognitive impairment (MCI) generally requires an evaluation of medical history and physical examination including neurological, neuropsychological, and psychiatric assessment, as well as various biological, radiological and electrophysiological tests, such as for instance measuring brain volume or activity measurements derived from neuroimaging modalities such as magnetic resonance imaging (MRI) or positron emission tomography (PET) of relevant brain regions. However, neuroimaging modalities are expensive, labor-intensive and not universally available. Despite the battery of tests available, a definitive diagnosis of AD can only be achieved by post-mortem brain examination. Thus there is a need for additional test and methods of assessing dementia and other cognitive disorders.

SUMMARY

The inventors have developed a method that can distinguish "dementia-relevant" variance in observed clinical and physiological measures from the variance in observed data that is unrelated to dementia, see "A LATENT VARIABLE APPROACH TO THE IDENTIFICATION AND/OR DIAGNOSIS OF COGNITIVE DISORDERS AND/OR BEHAVIORS AND THEIR ENDOPHENOTYPES" U.S. patent application Ser. No. 13/776,661 filed Feb. 25, 2013, which is incorporated herein by reference in its entirety. Furthermore, the inventors have used this methodology to identify biomarkers for the assessment of subjects. In certain aspects dementia is assessed in a non-Hispanic white subject using biomarkers identified using a latent variable approach. In other aspects, biomarker panels for clinical and pre-clinical Alzheimer's Disease in Hispanics, Asians, and other populations can be identified using the methods described herein.

The latent variable methods result in a d score that is an "error-free" continuously varying dementia endophenotype (i.e., "d") that can be used to make accurate clinical diagnoses from limited psychometric batteries, and can be used as an outcome in studies of potential biomarkers. The method is free of cultural, linguistic, or educational bias, and can be employed with very limited datasets, using either existing measures, or easily collected ones (e.g., telephone measures or brief screening tests).

The inventors have applied this methodology to data from the Texas Alzheimer's Research Consortium (TARCC) and have identified set of biomarkers for use in assessing subjects. In certain aspects, eleven serum proteins were identified as biomarkers, each of which is a significant independent predictor of the dementia endophenotype d. In their aggregate, they explain 25% of d's variance, independent of demographic covariates. In certain aspects various combinations of biomarkers can be used to assess and/or diagnose a subject. Moreover, the inventors have determined that ethnicity has a strong moderating effect on these associations such that certain biomarkers are not associated with d in the Mexican-American (MA) fraction of TARCC's cohort. In a further aspect biomarkers have been identified that are associated with d in Non-Hispanic Whites (NHW). In certain populations, the biomarkers alone or in various combinations accurately distinguish between normal controls and both Mild Cognitive Impairment (MCI) and Alzheimer's Disease (AD). The methods described can be used in various populations to identify biomarkers for a selected population. This can be accomplished by using a population specific group of subjects and assessing the selected population for distinguishing biomarkers by using a latent variable approach.

The d scores can be associated with serum biomarkers to identify biomarkers indicative of MCI. Six of the biomarkers described herein have been previously associated with clinical dementia in TARCC by traditional methods (O'Bryant et al., 2010; 2011a, 2011b). None were identified in previous efforts in other cohorts (Ray et al., 2007; Gomez Ravetti et al., 2008). None have been previously associated with MCI. One or more of these biomarkers accurately distinguish MCI from controls, i.e., they are altered in the earliest stages of the disease and are a useful diagnostic screening tool.

Neither MCI nor AD has previously been diagnosable solely on the basis of a panel of serum proteins. A simple blood test may be all that is required to make a diagnosis of AD, either in its clinical or pre-clinical stages.

Certain embodiments are directed to the methods of identifying pre-clinical subjects in the early stages of dementia using the measurement of one or more biomarkers. In certain aspects, a diagnosis of dementia can be confirmed or an ambiguous determination of dementia can be verified using the latent variable methods described herein. In certain aspects a subject is assessed or evaluated by measuring the levels of two or more biomarkers and determining if these levels are indicative of dementia. In certain aspects biomarker levels are measured in a blood or a serum sample.

In certain aspects, the biomarkers include 1, 2, 3, 4, 5, 6, 7, 8, 9, 10, or 11 biomarkers selected from IL-10, IL-12p40, IFN-γ, IL-13, α2 macroglobulin (A2M), β2 microglobulin (B2M), pancreatic polypeptide (pp), prolactin, stem cell factor (SCF), thrombopoietin, and Von Willebrand factor (vWF).

In certain aspects the biomarkers include IL-10 and 1, 2, 3, 4, 5, 6, 7, 8, or 9 biomarkers selected from IL-12p40, IFN-γ, IL-13, α2 macroglobulin (A2M), β2 microglobulin (B2M), pancreatic polypeptide (pp), prolactin, stem cell factor (SCF), thrombopoietin, and Von Willebrand factor (vWF).

In certain aspects the biomarkers include IL-12p40 and 1, 2, 3, 4, 5, 6, 7, 8, or 9 biomarkers selected from IL-10, IFN-γ, IL-13, α2 macroglobulin (A2M), β2 microglobulin (B2M), pancreatic polypeptide (pp), prolactin, stem cell factor (SCF), thrombopoietin, and Von Willebrand factor (vWF).

In certain aspects the biomarkers include IFN-γ and 1, 2, 3, 4, 5, 6, 7, 8, or 9 biomarkers selected from IL-10, IL-12p40, IL-13, α2 macroglobulin (A2M), β2 microglobulin (B2M), pancreatic polypeptide (pp), prolactin, stem cell factor (SCF), thrombopoietin, and Von Willebrand factor (vWF).

In certain aspects the biomarkers include IL-13 and 1, 2, 3, 4, 5, 6, 7, 8, or 9 biomarkers selected from IL-10, IL-12p40, IFN-γ, α2 macroglobulin (A2M), β2 microglobulin (B2M), pancreatic polypeptide (pp), prolactin, stem cell factor (SCF), thrombopoietin, and Von Willebrand factor (vWF).

In certain aspects the biomarkers include α2 macroglobulin (A2M) and 1, 2, 3, 4, 5, 6, 7, 8, or 9 biomarkers selected from IL-10, IL-12p40, IFN-γ, IL-13, β2 microglobulin (B2M), pancreatic polypeptide (pp), prolactin, stem cell factor (SCF), thrombopoietin, and Von Willebrand factor (vWF).

In certain aspects the biomarkers include 132 microglobulin (B2M) and 1, 2, 3, 4, 5, 6, 7, 8, or 9 biomarkers selected from IL-10, IL-12p40, IFN-γ, IL-13, α2 macroglobulin (A2M), pancreatic polypeptide (pp), prolactin, stem cell factor (SCF), thrombopoietin, and Von Willebrand factor (vWF).

In certain aspects the biomarkers include pancreatic polypeptide (pp) and 1, 2, 3, 4, 5, 6, 7, 8, or 9 biomarkers selected from IL-10, IL-12p40, IFN-γ, IL-13, α2 macroglobulin (A2M), 132 microglobulin (B2M), prolactin, stem cell factor (SCF), thrombopoietin, and Von Willebrand factor (vWF).

In certain aspects the biomarkers include prolactin and 1, 2, 3, 4, 5, 6, 7, 8, or 9 biomarkers selected from IL-10, IL-12p40, IFN-γ, IL-13, α2 macroglobulin (A2M), β2 microglobulin (B2M), pancreatic polypeptide (pp), stem cell factor (SCF), thrombopoietin, and Von Willebrand factor (vWF).

In certain aspects the biomarkers include stem cell factor (SCF) and 1, 2, 3, 4, 5, 6, 7, 8, or 9 biomarkers selected from IL-10, IL-12p40, IFN-γ, IL-13, α2 macroglobulin (A2M), 132 microglobulin (B2M), pancreatic polypeptide (pp), prolactin, thrombopoietin, and Von Willebrand factor (vWF).

In certain aspects the biomarkers include thrombopoietin and 1, 2, 3, 4, 5, 6, 7, 8, or 9 biomarkers selected from IL-10, IL-12p40, IFN-γ, IL-13, α2 macroglobulin (A2M), β2 microglobulin (B2M), pancreatic polypeptide (pp), prolactin, stem cell factor (SCF), and Von Willebrand factor (vWF).

In certain aspects the biomarkers include Von Willebrand factor (vWF) and 1, 2, 3, 4, 5, 6, 7, 8, or 9 biomarkers selected from IL-10, IL-12p40, IFN-γ, IL-13, α2 macroglobulin (A2M), β2 microglobulin (B2M), pancreatic polypeptide (pp), prolactin, stem cell factor (SCF), and thrombopoietin.

Certain embodiments are directed to methods of treating pre-clinical subjects for dementia once they have been identified using one or more biomarkers described herein. A pre-clinical subject is a subject that has not been clinically diagnosed with dementia. Clinical diagnosis for dementia case-finding is a consensus clinical diagnosis made by experienced clinicians with full access to comprehensive psychometric data, and employing standardized clinical diagnostic criteria (McKhann et al., 1984; Roman et al., 1993; McKeith et al., 1999; Winblad et al., 2004; Carins et al., 2007).

Certain embodiments are directed to a method for evaluating the effectiveness of a therapeutic comprising: (a) measuring the levels of one or more biomarker indicative of pre-clinical dementia in a subject; (b) administering a therapeutic to a subject; (c) measuring the levels of one or more biomarker indicative of pre-clinical dementia in a subject after administering a therapeutic; and (d) comparing the biomarker levels or the assessments based on the biomarker levels, wherein a relative change in the first and second assessment is indicative of the effectiveness of the therapeutic if the assessment improves or ineffectiveness if the assessment worsens.

As used herein, the term "biomarker" or "biochemical marker" refers to a protein, nucleic acid, or metabolite that is to be measured, detected, analyzed biochemically and/or monitored, for example, a small molecule, RNA, antigen, or antibody. In certain aspects, a biomarker is a serum protein.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen, e.g., three dimensional conformation or modification (e.g., phosphorylation), that gives rise to a biological response is referred to herein as an "antigenic determinant" or "epitope." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In certain aspects, Tau oligomers are utilized as antigens.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann (1990); Kostelny et al. (1992).

The reference level may comprise data obtained at the same time (e.g., in the same hybridization experiment) as the patient's individual data, or may be a stored value or set of values e.g. stored on a computer, or on computer-readable media. If the latter is used, new patient data for the selected marker(s), obtained from initial or follow-up samples, can be compared to the stored data for the same marker(s) without the need for additional control experiments.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Latent variables have been used to analyze cognitive batteries, but this has been limited to "g" and secondary factor studies containing only one type of indicator variables (i.e., cognitive measures or functional status measures only). Similarly, although biomarkers have been sought in AD cohorts, only clinical diagnoses have been used as outcomes (i.e., Ray et al., 2007; Gomez Ravetti & Moscato, 2008, O'Bryant et al., 2010, 2011a; 2011b), never latent variable proxies for clinical diagnoses.

As a latent variable, d's existence may not be obvious to clinicians and researchers because it cannot be directly measured. Moreover, the latent construct represented by d comprises only a fraction of the variance in each measure's raw score. This aspect is generic to all d-homologs. Beyond these generic considerations, it is unconventional to mix predictors and potential target measures as indicators of the same latent construct. The only comparable application the inventors are aware of in the SEM literature is Palmer et al.'s (2002) use of an analogous hybrid construct to adjust latent variable indicators for potential bias effects. The inventor's insight was to use a hybrid construct as the variable of interest itself. This is a qualitative conceptual advance over Palmer's earlier application.

Efforts to associate clinical diagnoses with a wide range of biomarkers have been hampered by so-called "batch" effects (IOM, 2012). Serum biomarker levels may vary as a function of the case-mix across sample processing batches, but it is difficult to account for technical measurement error. The inventors have overcome this in an SEM framework by adjusting observed biomarker values for demographic adjusted batch values. This cannot be effected in traditional parametric and non-parametric regression models.

Moreover, the approach results in a continuously varying, error-free dementia endophenotype. This is much more statistically robust than diagnostic categories, which are categorical, and prone to measurement error. Studies can be conducted with improved power, larger sample sizes, and in minority or difficult to assess target populations.

I. Biomarkers

Certain aspects of the methods described identify serum markers for cognitive disorders such as Alzheimer's disease, allowing the development of effective and predictive diagnostics for the presence, degree of severity/advancement or risk of developing such disease. The invention describes the identification of molecular signatures specifically or preferentially expressed in the blood of patients developing a cognitive disorder. The methods provide tools and methods for diagnosing, predicting and/or monitoring the progression of cognitive disorders, based on measuring the level of biomarkers in the subjects' blood. The presence of elevated levels of biomarkers allows the identification, risk of, or predisposition to cognitive disorders, or confirming the presence of such disorders in a subject.

The term "level" refers to the amount or concentration of a biomarker molecule. A level can be represented, for example, by the a molecule such as a polypeptide. The term can be used to refer to an absolute amount of a molecule in a sample or to a relative amount of the molecule, including amounts or concentration determined under steady-state or non-steady-state conditions. Level may also refer to an assay signal that correlates with the amount or concentration of a biomarker molecule. The level of a molecule can be determined relative to a control molecule in a sample. According to one aspect, the level(s) of biomarker(s) are measured in the samples collected from individuals suspected of or at risk of developing a condition associated with dementia.

TARCC has collected a wide range of serum and genetic biomarkers on its subjects, as well as longitudinal clinical assessments. O'Bryant et al. (2010; 2011a) have identified the set of serum biomarkers that are associated with clinical diagnoses in TARCC, and validated a subset of these in a second cohort (O'Bryant et al., 2011b). However, dementia's clinical diagnosis is an inefficient art. Many features of the clinical exam are ill-defined and/or subjectively assessed. Clinicians differ widely in their training, skills, and dementia-assessment experience. Patients vary substantially in their presentations, often because of comorbid conditions, concurrent medications, educational, cultural, and/or linguistic differences. Finally, clinicians are per force ill equipped to assess the "pre-clinical" stages of disease, where interventions could have their greatest impact. As a result, there is considerable "measurement error" in statistical models that use clinical diagnosis as an outcome, and this risk to undermine the validity of the biomarkers that are rapidly being associated with those outcomes.

As a result of the latent variable methods developed by the inventors, a set of AD serum biomarkers has been identified. Six of the biomarkers have been previously associated with clinical dementia in TARCC by traditional methods (O'Bryant et al., 2010; 2011a, 2011b). Thus, the latent variable approach has identified new biomarkers even when traditional techniques are applied to the same dataset. Moreover, none of the biomarkers were identified in previous diagnosis-based efforts in other cohorts (Ray et al., 2007; Gomez Ravetti et al., 2008). None of the biomarkers have been previously associated with mild cognitive impairment (MCI).

One or more of the biomarkers distinguish MCI from controls, i.e., they are altered in the earliest stages of AD. They appear to mark the onset of the disorder, but distinguish less well between MCI and AD. Moreover, they are strongly related to ethnicity. Certain biomarkers are less relevant to dementing illness in Mexican American (MA) cases. This suggests that clinical "AD" in MA persons may be the result of a distinct biological mechanism.

Biomarkers can be used to both define a disease state as well as to provide a means to predict physiological and clinical manifestations of a disease. Three commonly discussed ways in which biomarkers could be used clinically are: (1) to characterize a disease state, i.e. establish a diagnosis, (2) to demonstrate the progression of a disease, and (3) to predict the progression of a disease, i.e. establish a prognosis. Establishing putative biomarkers for such uses typically requires a statistical analysis of relative changes in biomarker expression either cross-sectionally and/or over time (longitudinally). For example, in a state or diagnostic biomarker analysis, levels of one or more biomarkers are measured cross-sectionally, e.g. in patients with disease and in normal control subjects, at one point in time and then related to the clinical status of the groups. Statistically significant differences in biomarker expression can be linked to presence or absence of disease, and would indicate that the biomarkers could subsequently be used to diagnose patients as either having disease or not having disease. In a progression analysis, levels of one or more biomarkers and clinical status are both measured longitudinally. Statistically significant changes over time in both biomarker expression and clinical status would indicate that the biomarkers under study could be used to monitor the progression of the disease. In a prognostic analysis, levels of one or more biomarkers are measured at one point in time and related to the change in clinical status from that point in time to another subsequent point in time. A statistical relationship between biomarker expression and subsequent change in clinical status would indicate that the biomarkers under study could be used to predict disease progression.

Results from prognostic analyses can also be used for disease staging and for monitoring the effects of drugs. The prediction of variable rates of decline for various groups of patients allows them to be identified as subgroups that are differentiated according to disease severity (i.e. less versus more) or stage (i.e. early versus late). Also, patients treated with a putative disease-modifying therapy may demonstrate an observed rate of cognitive decline that does not match the rate of decline predicted by the prognostic analysis. This could be considered evidence of drug or treatment efficacy.

Certain embodiments are directed to assessing a subject by measuring the levels of 1, 2, 3, 4, 5, 6, 7, 8, 9, 10, 11, or more biomarkers and determining if these levels are indicative of dementia, early stage dementia, Alzheimer's Disease (AD) or early stage AD. In certain aspects, the biomarkers include 1, 2, 3, 4, 5, 6, 7, 8, 9, 10, or 11 biomarkers selected from IL-10, IL-12p40, IFN-γ, IL-13, α2 macroglobulin (A2M), microglobulin (B2M), pancreatic polypeptide (pp), prolactin, stem cell factor (SCF), thrombopoietin, and Von Willebrand factor (vWF). In certain aspects, the biomarkers can include any 2, 3, 4, 5, 6, 7, 8, 9, 10 or 11 of IL-10, IL-12p40, IFN-γ, IL-13, α2 macroglobulin (A2M), β2 microglobulin (B2M, pancreatic polypeptide (pp), prolactin, stem cell factor (SCF), thrombopoietin, and Von Willebrand factor (vWF). In further aspects, the biomarkers assessed include IL-10, IL-12p40, IFN-γ, IL-13, α2 macroglobulin (A2M), β2 microglobulin (B2M, pancreatic polypeptide (pp), prolactin, stem cell factor (SCF), thrombopoietin, and Von Willebrand factor (vWF).

Interleukin-10 (IL-10 or IL10), also known as human cytokine synthesis inhibitory factor (CSIF), is an anti-inflammatory cytokine. In humans IL-10 has an amino acid sequence as provided in GenBank accession No. NP_000563.1, which is incorporated herein by reference. This cytokine is produced primarily by monocytes and to a lesser extent by lymphocytes. It has pleiotropic effects in immunoregulation and inflammation and down-regulates the expression of Th1 cytokines, MHC class II antigens, and costimulatory molecules on macrophages. It also enhances B cell survival, proliferation, and antibody production.

Subunit beta of interleukin 12 has an amino acid sequence as provided in GenBank accession No. NP_002178.2, which is incorporated herein by reference, (also known as natural killer cell stimulatory factor 2, or cytotoxic lymphocyte maturation factor 2, IL12p40) and is a subunit of human interleukin 12. This polypeptide is a subunit of interleukin 12, a cytokine that acts on T and natural killer cells, and has a broad array of biological activities. Interleukin 12 is a disulfide-linked heterodimer composed of the 40 kD cytokine receptor like subunit and a 35 kD subunit encoded by IL12A. It is expressed by activated macrophages that serve as an essential inducer of Th1 cells development. This cytokine has been found to be important for sustaining a sufficient number of memory/effector Th1 cells to mediate long-term protection to an intracellular pathogen.

Interferon-gamma (IFN-γ) is a dimeric soluble cytokine that is the only member of the type II class of interferons. The IFN-γ protein has an amino acid sequence as provided in GenBank accession No. NP_000610.2, which is incorporated herein by reference. IFN-γ, or type II interferon, is a cytokine that is critical for innate and adaptive immunity against viral and intracellular bacterial infections and for tumor control. Aberrant IFN-γ expression is associated with a number of autoinflammatory and autoimmune diseases. The importance of IFN-γ in the immune system stems in part from its ability to inhibit viral replication directly, and most importantly from its immunostimulatory and immunomodulatory effects. IFN-γ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops.

Interleukin 13 (IL-13) is a protein having an amino acid sequence provided in GenBank accession No. NP_002179.2, which is incorporated herein by reference. IL-13 is cytokine secreted by many cell types, but especially T helper type 2 (Th2) cells. In addition to effects on immune cells, IL-13 is implicated as a central mediator of the physiologic changes induced by allergic inflammation in many tissues. IL-13 induces its effects through a multi-subunit receptor that includes the alpha chain of the IL-4 receptor (IL-4Rα) and at least one of two known IL-13-specific binding chains.

Alpha-2-Macroglobulin, also known as α2-macroglobulin and abbreviated as α2M and A2M, is a large plasma protein found in the blood (see GenBank accession No. NPM_000005.2 for the amino acid sequence of A2M). It is produced primarily by the liver, and is a major component of the alpha-2 band in protein electrophoresis. Alpha 2-Macroglobulin is the largest major non-immunoglobulin protein in plasma. Alpha 2 macroglobulin acts as an anti-protease and is able to inactivate an enormous variety of proteinases. It functions as an inhibitor of fibrinolysis by inhibiting plasmin and kallikrein. It functions as an inhibitor of coagulation by inhibiting thrombin. Alpha 2-macroglobulin may act as a carrier protein because it also binds to numerous growth factors and cytokines, such as platelet-derived growth factor, basic fibroblast growth factor, TGF-β, insulin, and IL-1β.

β2 microglobulin also known as B2M is a component of MHC class I molecules, which are present on all nucleated cells (excluding red blood cells). In humans, the β2 microglobulin protein has an amino acid sequence of the provided in GenBank accession No. NP_004039.1, which is incorporated here by reference. β2 microglobulin associates not only with the alpha chain of MHC class I molecules, but also with class I-like molecules such as CD1 and Qa.

Pancreatic polypeptide (PP) is a polypeptide secreted by PP cells in the endocrine pancreas predominantly in the head of the pancreas. It consists of 36 amino acids and has molecular weight about 4200 Da (see GenBank accession No. NP_002713.1, which is incorporated herein by reference). The function of PP is to self regulate pancreatic secretion activities (endocrine and exocrine), it also has effects on hepatic glycogen levels and gastrointestinal secretions.

Prolactin (PRL) also known as luteotropic hormone (LTH) is a protein having an amino acid sequence as provided in GenBank accession No. NP_000948.5, which is incorporated herein by reference. Prolactin acts in a cytokine-like manner and as an important regulator of the immune system. Prolactin has important cell cycle related functions as a growth-, differentiating- and anti-apoptotic factor. As a growth factor binding to cytokine like receptors it has also profound influence on hematopoiesis, angiogenesis and is involved in the regulation of blood clotting through several pathways.

Stem Cell Factor (also known as SCF, kit-ligand, KL, or steel factor) is a cytokine that binds to the c-Kit receptor (CD117)(see GenBank accession No. NP_000890.1, which is incorporated herein by reference). SCF can exist both as a transmembrane protein and a soluble protein. This cytokine plays an important role in hematopoiesis (formation of blood cells), spermatogenesis, and melanogenesis.

Thrombopoietin (THPO) also known as megakaryocyte growth and development factor (MGDF) is a protein having an amino acid sequence provided by GenBank accession No. NP_000451.1, which is incorporated herein by reference. Thrombopoietin is a glycoprotein hormone produced mainly by the liver and the kidney that regulates the production of platelets by the bone marrow. It stimulates the production and differentiation of megakaryocytes, the bone marrow cells that fragment into large numbers of platelets.

Von Willebrand factor (vWF) is a blood glycoprotein involved in hemostasis, See GenBank accession No. NP_000543.2, which incorporated herein by reference. It is deficient or defective in von Willebrand disease and is involved in a large number of other diseases, including thrombotic thrombocytopenic purpura, Heyde's syndrome, and possibly hemolytic-uremic syndrome.

Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics.

In certain aspects immunoassays include, for example, sandwich immunoassays including ELISA or fluorescence-based immunoassays, as well as other enzyme immunoassays. In the SELDI-based immunoassay, a biospecific capture reagent for the biomarker is attached to a surface, such as a pre-activated ProteinChip array. The biomarker is then specifically captured on the biochip through this reagent, and the captured biomarker is detected by mass spectrometry.

II. Latent Variable Methods

Methods employing a latent variable are described in U.S. patent application Ser. No. 13/776,661 filed Feb. 25, 2013 entitled "A LATENT VARIABLE APPROACH TO THE IDENTIFICATION AND/OR DIAGNOSIS OF COGNITIVE DISORDERS AND/OR BEHAVIORS AND THEIR ENDOPHENOTYPES," which is incorporated herein by reference in its entirety. The latent variable methodology can distinguish "target-relevant" variance in observed clinical and physiological measures from the variance in observed data that is unrelated to any target process. The approach has been validated in the context of dementia assessment and is applicable to other cognitive and/or functional assessments. In the case of dementia, the method results in a latent variable or score, "d" (dementia-relevant variance in cognitive task performance), that represents only a small fraction of the total variance in observed cognitive task performance, yet is strongly associated with clinicians' assessments of dementia status and severity. The variable d correlates strongly (partial r=0.80-0.96) with current consensus dementia severity measures (i.e., the Clinical Dementia Rating Scale (CDR) (Hughes et al., 1982), and is highly accurate in predicting the consensus clinical diagnoses of experienced clinicians [Receiver Operating Curve (ROC) Area Under the Curve (AUC)=0.96-0.99 for the discrimination between Alzheimer's Disease (AD) and controls].

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Serum Biomarkers Associated with D Scores

A. Results

The inventors recently reconceptualized dementia as "the cognitive correlates of functional status" (Royall et al., 2007; Royall, Palmer & O'Bryant, in press). This construct can be operationally defined by a latent variable, i.e., "d", in a Structural Equation Model (SEM) environment (Bryne, 2001). The inventors have successfully constructed d and validated it in three different cohorts. The latent variable d is strongly related to Clinical Dementia Rating scale (CDR) scores (Hughes et al., 1982) performed blind by clinicians (Royall, Palmer & O'Bryant, in press; Royall et al. in review) and achieves very high Areas Under the Receiver Operating Curve (AUC; ROC) for the discriminations between AD and controls (AUC range 0.987-995) and Mild Cognitive Impairment (MCI) (AUC range 0.950-0.957).

The inventors recently validated d in the Texas Alzheimer's Research and Care Consortium (TARCC) cohort and tested its ability to discriminate controls from cases with MCI (Royall & Palmer, unpublished manuscript). Unfortunately, d's AUC for this discrimination was less impressive (AUC=0.785). This was likely due to floor effects in its functional status indicators. Nevertheless, d scores can predict longitudinal cognitive decline among initially non-demented persons (Royall & Palmer, 2012).

One of the many advantages of using latent variables for dementia case finding is that d's factor scores can be used to generate a continuously varying dementia endophenotype. This can then be associated with biomarkers using powerful parametric statistical methods. The inventors recently demonstrated that d scores are specifically associated with grey matter atrophy in the Default Mode Network (DMN). That network is specifically affected by beta-amyloid deposition early in AD's natural history and tangle pathology in its hubs is strongly associated with clinical dementia (Buckner et al., 2005, Royall et al., 2002).

d scores accurately distinguish between AD and controls, MCI and between controls and either MCI or AD, but are less accurate in distinguishing between controls and MCI.

TABLE 1

ROC Analysis of d as a Predictor of Adjudicated Clinical Dementia Status
Area Under the Curve

| Test Result Variable(s) | AUC |
| --- | --- |
| AD v. Controls | 0.978 |
| AD v. MCI | 0.914 |
| Controls v. all others | 0.901 |
| MCI v. Controls | 0.783 |

To overcome d's relatively poor discrimination between controls and cases of MCI, the inventors exchanged CDR-SB for IADL in d's model. This amended d retains the original's excellent AUC's for AD v. control, AD v. MCI and controls v. all others, but also has improved potential to distinguish controls from MCI (AUC=0.83) (Table 2).

TABLE 2

ROC Analysis of the Revised d as a Predictor of TARCC Adjudicated
Clinical Dementia Status
Area Under the Curve

| Test Result Variable(s) | Area |
| --- | --- |
| AD v. Controls | 0.989 |
| AD v. MCI | 0.938 |
| Controls v. all others | 0.926 |
| MCI v. Controls | 0.830 |

Having validated this new model, the inventors proceeded to test 21 serum biomarkers as predictors of d. All had been previously identified by O'Bryant et al. (2010) as predictors of clinical diagnoses in TARCC. However, only 11 are confirmed as independent predictors of d scores.

TABLE 3

Demographic, Selected Cytokine and Potential Serum Biomarker Predictors of d scores $R^2 = 0.45$; N = 2016

|  | β | b | SE b | p-value |
|---|---|---|---|---|
| Age | −0.139 | −0.012 | 0.002 | ≤0.001 |
| Education | 0.245 | 0.052 | 0.006 | ≤0.001 |
| Ethnicity | 0.157 | 0.287 | 0.061 | ≤0.001 |
| APOE Status | −0.232 | −0.376 | 0.049 | ≤0.001 |
| IL-5 | −0.053 | −0.011 | 0.008 | 0.168 |
| IL-10 | 0.104 | 0.015 | 0.006 | 0.006 |
| IL-12p40 | −0.096 | −0.445 | 0.194 | 0.022 |
| IFN-γ | 0.077 | 0.037 | 0.015 | 0.011 |
| IL-13 | 0.227 | 0.004 | 0.001 | ≤0.001 |
| α-2 Macroglobulin | −0.278 | −0.151 | 0.017 | ≤0.001 |
| β-2 Macroglobulin | 0.090 | 0.70 | 0.028 | 0.012 |
| C-Reactive Protein | 0.012 | 0.002 | 0.006 | 0.695 |
| Creatine Kinase-MB | −0.016 | −0.012 | 0.023 | 0.615 |
| Eotaxin-3 | 0.000 | 0.000 | 0.000 | 0.995 |
| FAS Ligand | 0.035 | 0.000 | 0.000 | 0.214 |
| ICAM-1 | −0.005 | 0.000 | 0.000 | 0.881 |
| MIP1-α | 0.015 | 0.000 | 0.000 | 0.578 |
| Pancreatic Polypeptide | −0.065 | 0.000 | 0.000 | 0.025 |
| Prolactin | −0.084 | −0.011 | 0.004 | 0.006 |
| Prostatic Acid Phosphatase | 0.005 | 0.006 | 0.032 | 0.858 |
| Resistin | −0.057 | −0.044 | 0.028 | 0.120 |
| S100b | −0.006 | −0.016 | 0.081 | 0.848 |
| Stem Cell Factor | 0.138 | 0.001 | 0.000 | ≤0.001 |
| Thrombopoietin | −0.129 | −0.065 | 0.026 | 0.011 |
| TNF-β | −0.008 | −0.001 | 0.004 | 0.782 |
| Von Willebrand Factor | −0.071 | −0.002 | 0.001 | 0.020 |

Fit Indicies:
$\chi^2$CMIN/DF = 2.11, p < 0.001
CFI = 0.988
RMSEA = 0.023

TABLE 4

Demographic and Cytokine Predictors of d scores $R^2 = 0.33$ $F(17,463) = 13.41$, p ≤ 0.001; N = 481

|  | β | SE β | b | SE b | t(460) | p-value |
|---|---|---|---|---|---|---|
| Intercept |  |  | 1.435 | 0.228 | 6.298 | ≤0.001 |
| Age | −0.186 | 0.041 | −0.012 | 0.003 | −4.547 | ≤0.001 |
| Education | 0.312 | 0.041 | 0.054 | 0.007 | 7.696 | ≤0.001 |
| Apoe e4 status | −0.130 | 0.039 | −0.182 | 0.055 | −3.325 | 0.001 |
| IFN-γ | 0.126 | 0.044 | 0.043 | 0.015 | 2.864 | 0.004 |
| TNF-α | −0.024 | 0.047 | −0.001 | 0.002 | −0.511 | 0.609 |
| TNF-β | −0.006 | 0.042 | −0.001 | 0.004 | −0.143 | 0.886 |
| IL-1ra | −0.031 | 0.041 | −0.000 | 0.000 | −0.760 | 0.448 |
| IL-3 | 0.214 | 0.110 | 0.744 | 0.384 | 1.936 | 0.053 |
| IL-5 | −0.051 | 0.059 | −0.008 | 0.009 | −0.866 | 0.387 |
| IL-7 | 0.020 | 0.097 | 0.000 | 0.001 | 0.206 | 0.837 |
| IL-8 | 0.018 | 0.045 | 0.001 | 0.003 | 0.408 | 0.683 |
| IL-10 | 0.165 | 0.062 | 0.017 | 0.006 | 2.671 | 0.008 |
| IL-12p40 | −0.132 | 0.064 | −0.402 | 0.194 | −2.072 | 0.039 |
| IL-13 | 0.061 | 0.143 | 0.001 | 0.002 | 0.429 | 0.668 |
| IL-15 | −0.112 | 0.079 | −0.184 | 0.130 | −1.413 | 0.158 |
| IL-16 | 0.060 | 0.056 | 0.000 | 0.000 | 1.084 | 0.279 |
| IL-18 | 0.022 | 0.041 | 0.000 | 0.000 | 0.546 | 0.585 |

TABLE 5

Demographic and Cytokine Predictors of d scores $R^2 = 0.38$ $F(26,454) = 10.66$, p ≤ 0.001; N = 481

|  | β | SE β | b | SE b | t(454) | p-value |
|---|---|---|---|---|---|---|
| Intercept |  |  | 1.678 | 0.246 | 6.819 | ≤0.001 |
| Age | −0.157 | 0.045 | −0.010 | 0.003 | −3.472 | 0.001 |
| Education | 0.284 | 0.041 | 0.049 | 0.007 | 6.894 | ≤0.001 |
| Apoe e4 status | −0.153 | 0.039 | −0.215 | 0.054 | −3.943 | ≤0.001 |
| IFN-γ | 0.128 | 0.045 | 0.043 | 0.015 | 2.873 | 0.004 |
| IL-10 | 0.218 | 0.053 | 0.023 | 0.006 | 4.151 | ≤0.001 |
| IL-12p40 | −0.064 | 0.049 | −0.194 | 0.150 | −1.297 | 0.195 |
| α2-Macroglobulin | −0.005 | 0.040 | −0.003 | 0.023 | −0.115 | 0.909 |
| β2-Microglobulin | 0.058 | 0.052 | 0.042 | 0.038 | 1.104 | 0.270 |
| C-Reactive Protein | −0.004 | 0.044 | −0.001 | 0.006 | −0.097 | 0.923 |
| Creatine Kinase-MB | −0.023 | 0.046 | −0.014 | 0.029 | −0.497 | 0.620 |
| Eotaxin-3 | 0.013 | 0.039 | 0.000 | 0.000 | 0.332 | 0.740 |
| Fas Ligand | 0.057 | 0.038 | 0.000 | 0.000 | 1.503 | 0.134 |
| G-CSF | −0.063 | 0.054 | −0.006 | 0.005 | −1.177 | 0.240 |
| ICAM-1 | −0.025 | 0.046 | −0.000 | 0.001 | −0.543 | 0.588 |
| IGF BP-2 | −0.014 | 0.051 | −0.000 | 0.001 | −0.278 | 0.781 |
| MIP-1α | 0.014 | 0.038 | 0.000 | 0.000 | 0.365 | 0.715 |
| Pancreatic polypeptide | −0.051 | 0.039 | −0.000 | 0.000 | −1.300 | 0.194 |
| Prolactin | −0.069 | 0.045 | −0.008 | 0.005 | −1.543 | 0.124 |
| Prostatic Acid Phosphatase | 0.009 | 0.041 | 0.006 | 0.027 | 0.226 | 0.822 |
| Resistin | −0.111 | 0.057 | −0.068 | 0.035 | −1.945 | 0.052 |
| S100b | −0.028 | 0.042 | −0.053 | 0.079 | −0.673 | 0.501 |
| Stem Cell Factor | 0.234 | 0.054 | 0.001 | 0.000 | 4.356 | ≤0.001 |
| Tenascin-C | 0.026 | 0.044 | 0.000 | 0.000 | 0.585 | 0.559 |
| Thrombopoietin | −0.193 | 0.071 | −0.061 | 0.022 | −2.720 | 0.007 |
| VCAM-1 | −0.046 | 0.051 | −0.000 | 0.000 | −0.891 | 0.373 |
| Von Willebrand Factor | −0.104 | 0.043 | −0.002 | 0.001 | −2.427 | 0.016 |

TABLE 6

Regression Summary for Dependent Variable: dCDR (Tarcw1)
R = .70859149 $R^2$ = .50210190 Adjusted $R^2$ = .49182419 F(9,436) = 48.853 N = 446 AD excluded.

|  | b* | Std. Err. - of b* | b | Std. Err. - of b | t(436) | p-value |
|---|---|---|---|---|---|---|
| Intercept |  |  | 1.06 | 0.14 | 7.39 | 0.00 |
| Stem_Cell_Factor | 0.15 | 0.05 | 0.00 | 0.00 | 3.10 | 0.00 |
| Thrombopoietin | 0.22 | 0.06 | 0.05 | 0.02 | 3.57 | 0.00 |
| Resistin | −0.19 | 0.04 | −0.09 | 0.02 | −4.33 | 0.00 |
| apoe_status | −0.07 | 0.03 | −0.08 | 0.04 | −2.01 | 0.04 |
| IL_10 | 0.13 | 0.05 | 0.01 | 0.00 | 2.95 | 0.00 |
| IL_12p40 | −0.16 | 0.04 | −0.36 | 0.10 | −3.62 | 0.00 |
| IFN_gamma | 0.12 | 0.04 | 0.03 | 0.01 | 3.31 | 0.00 |
| AgeAtVisit | −0.06 | 0.04 | −0.00 | 0.00 | −1.61 | 0.11 |
| EDUC | 0.31 | 0.04 | 0.04 | 0.00 | 8.46 | 0.00 |

TABLE 7

Regression Summary for Dependent Variable: dCDR (Tarcw1)
R = .56175159 $R^2$ = .31556485 Adjusted $R^2$ = .27449874 F(9,150) = 7.6843 n = 160 Controls excluded.

|  | b* | Std. Err. - of b* | b | Std. Err. - of b | t(150) | p-value |
|---|---|---|---|---|---|---|
| Intercept |  |  | 0.765 | 0.453 | 1.689 | 0.093 |
| Stem_Cell_Factor | −0.056 | 0.080 | −0.000 | 0.000 | −0.696 | 0.487 |
| Thrombopoietin | −0.399 | 0.091 | −0.142 | 0.032 | −4.386 | 0.000 |
| Resistin | 0.115 | 0.079 | 0.076 | 0.052 | 1.465 | 0.145 |
| apoe_status | −0.053 | 0.072 | −0.069 | 0.093 | −0.739 | 0.461 |
| IL-10 | −0.012 | 0.071 | −0.003 | 0.018 | −0.174 | 0.862 |
| IL_12p40 | 0.035 | 0.075 | 0.125 | 0.266 | 0.469 | 0.640 |
| IFN_gamma | 0.053 | 0.073 | 0.028 | 0.039 | 0.722 | 0.471 |
| AgeAtVisit | −0.061 | 0.073 | −0.005 | 0.005 | −0.838 | 0.404 |
| EDUC | 0.305 | 0.071 | 0.055 | 0.013 | 4.316 | 0.000 |

Figure 1:
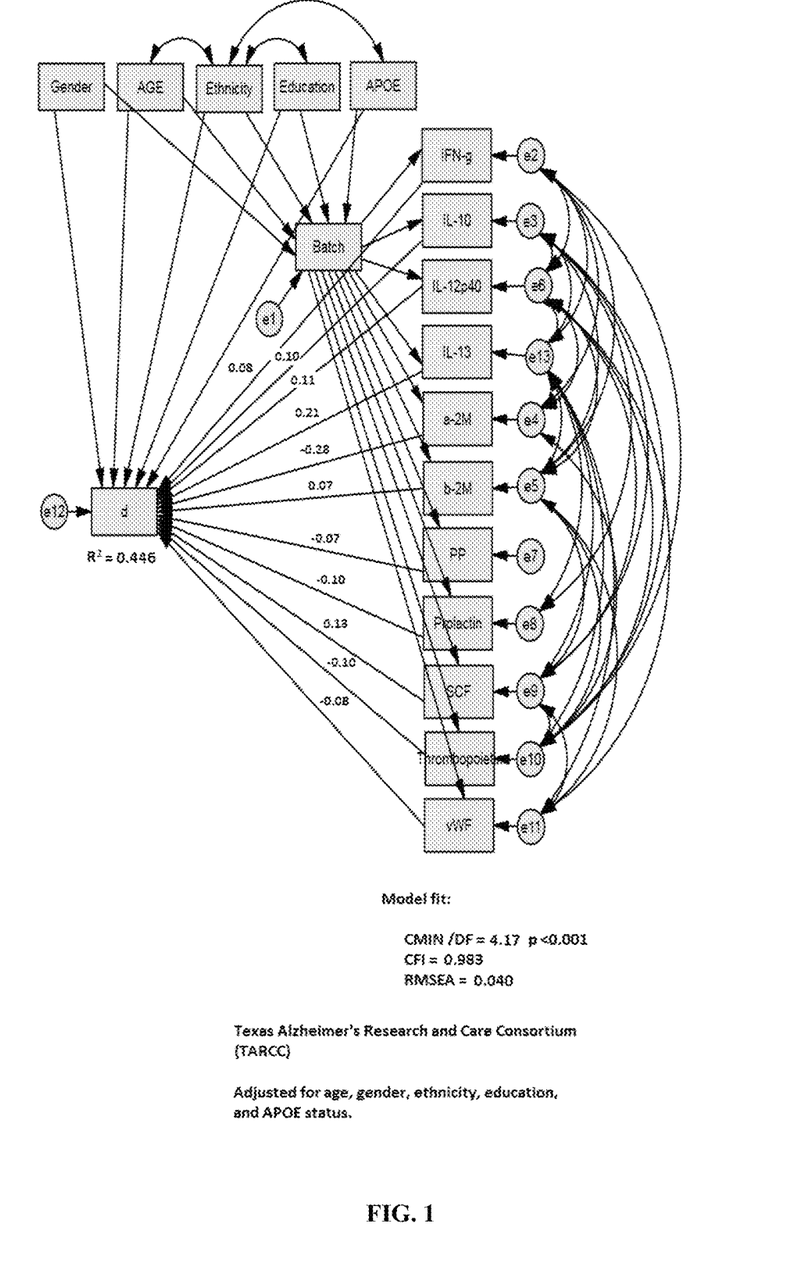
FIG. 1. Serum Proteins Associated with d Scores. APOE=apolipoprotein e4 status; IFN-☐=gamma interferon; IL-10=interleukin-10; ☐-2M=alpha-macroglobulin; PP=pancreatic polypeptide; SCF=stem cell factor; vWF=von Willebrand Factor. *Adjusted for age, gender, ethnicity, education, and APOE e4 status. Serum biomarkers are additionally adjusted for demographic adjusted batch effect. $R^2$=0.44, N=2016.

The final model (FIG. 1) explains 45% of d's variance. 25% is explained by the biomarkers, independent of covariates. The selected proteins are highly inter-correlated with the single exception of pancreatic polypeptide (PP). This suggests they represent a coordinated inflammatory response (and that PP does not contribute to it). All 11 can be related to "innate immunity", a host defense against microbiological invasion. This suggests a potential mechanism for the variability in d scores, and hence clinical dementia status in TARCC. It also suggests an infectious etiology for AD.

Figure 2:
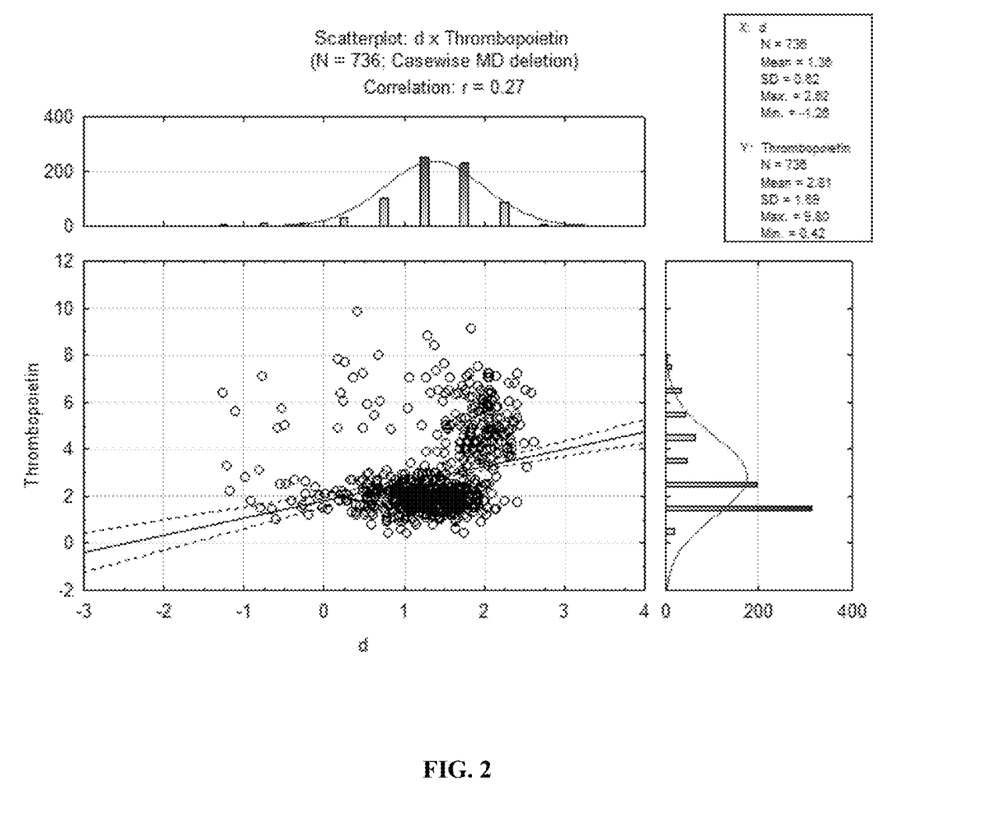
FIG. 2. Thrombopoietin x d Score Scatterplot.

However, visual inspection of individual biomarker x d score scatterplots suggest two populations [e.g., thrombopoietin (TPO) below (FIG. 2)].

Figure 3:
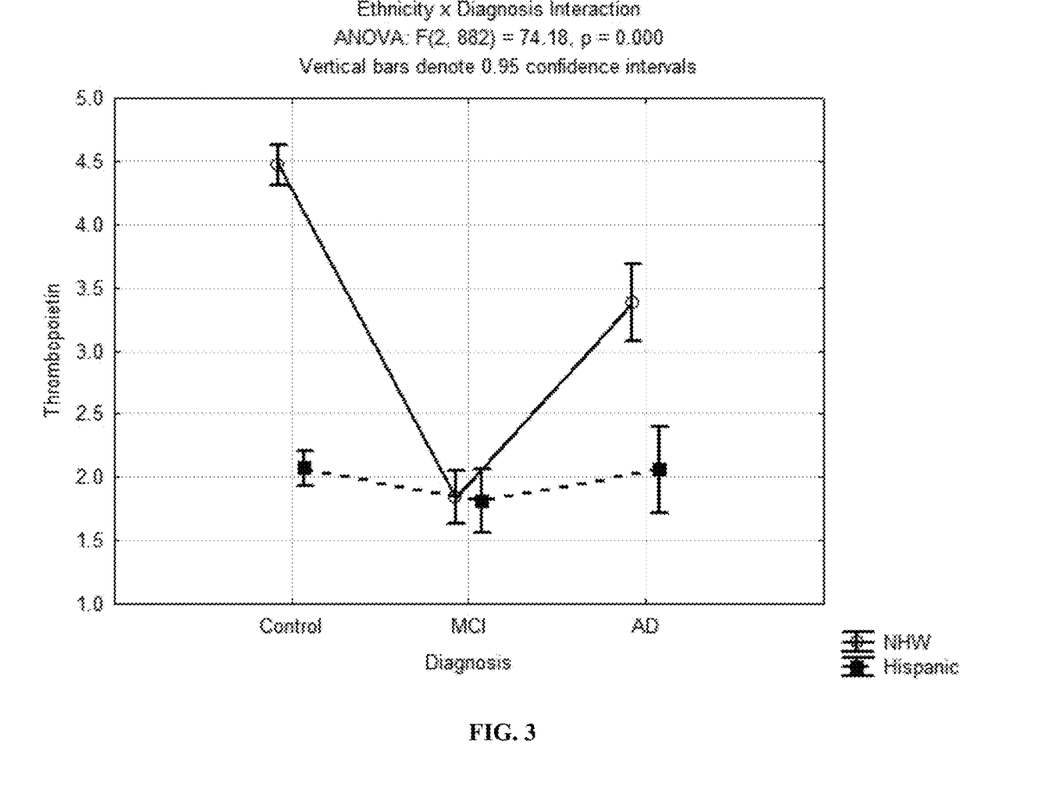
FIG. 3. Ethnicity by Diagnosis Interaction in Serum TPO Levels.

Since TARCC is composed largely of MA Hispanics and NHW, the inventors tested for ethnicity x diagnosis interactions and found significant effects on each of the selected biomarkers (by ANOVA) (FIG. 3).

Figure 4:
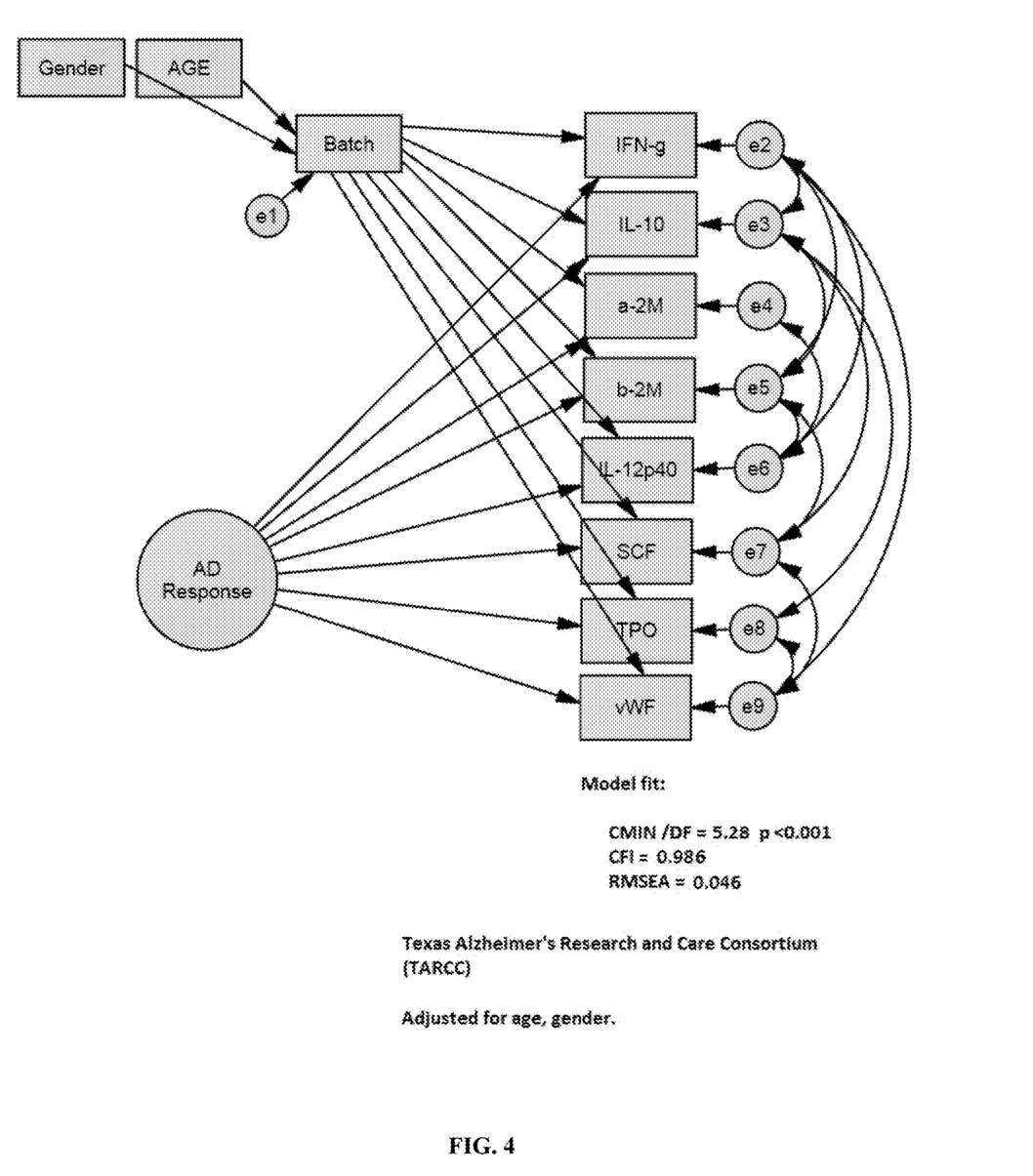
FIG. 4. Final Predictive Model.
Figure 5:
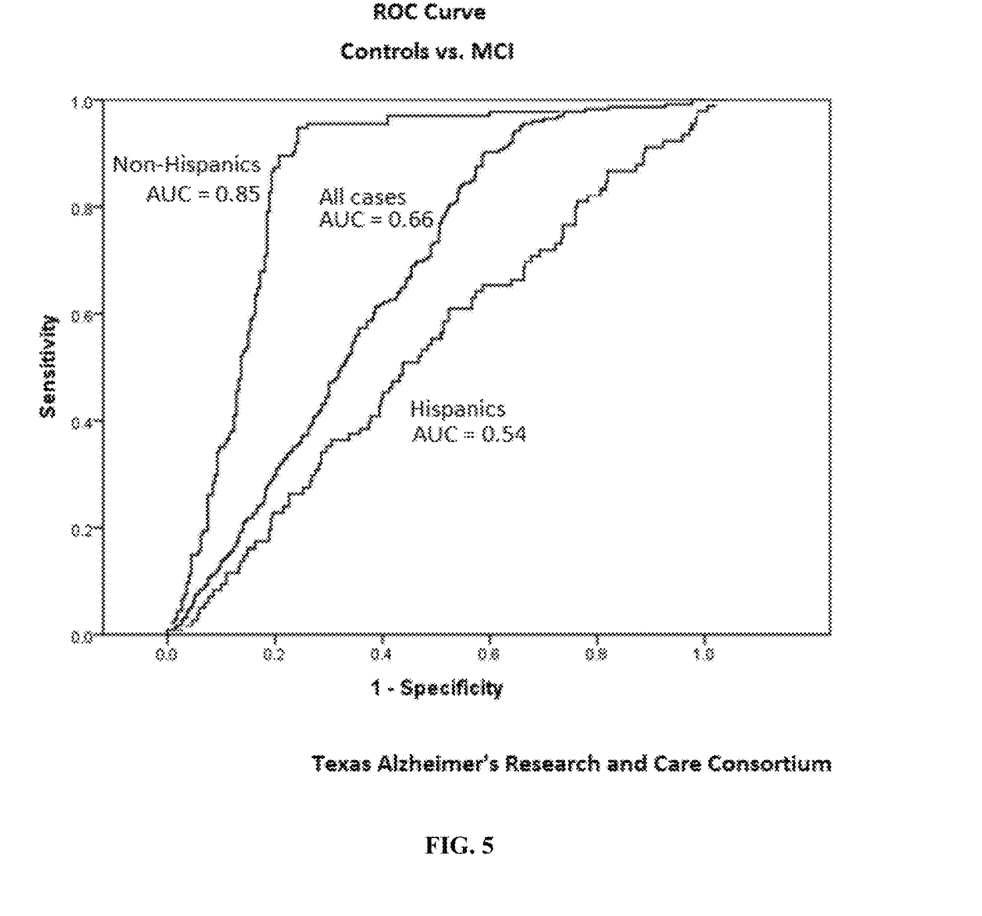
FIG. 5. ROC curve Controls vs. MCI.
Figure 6:
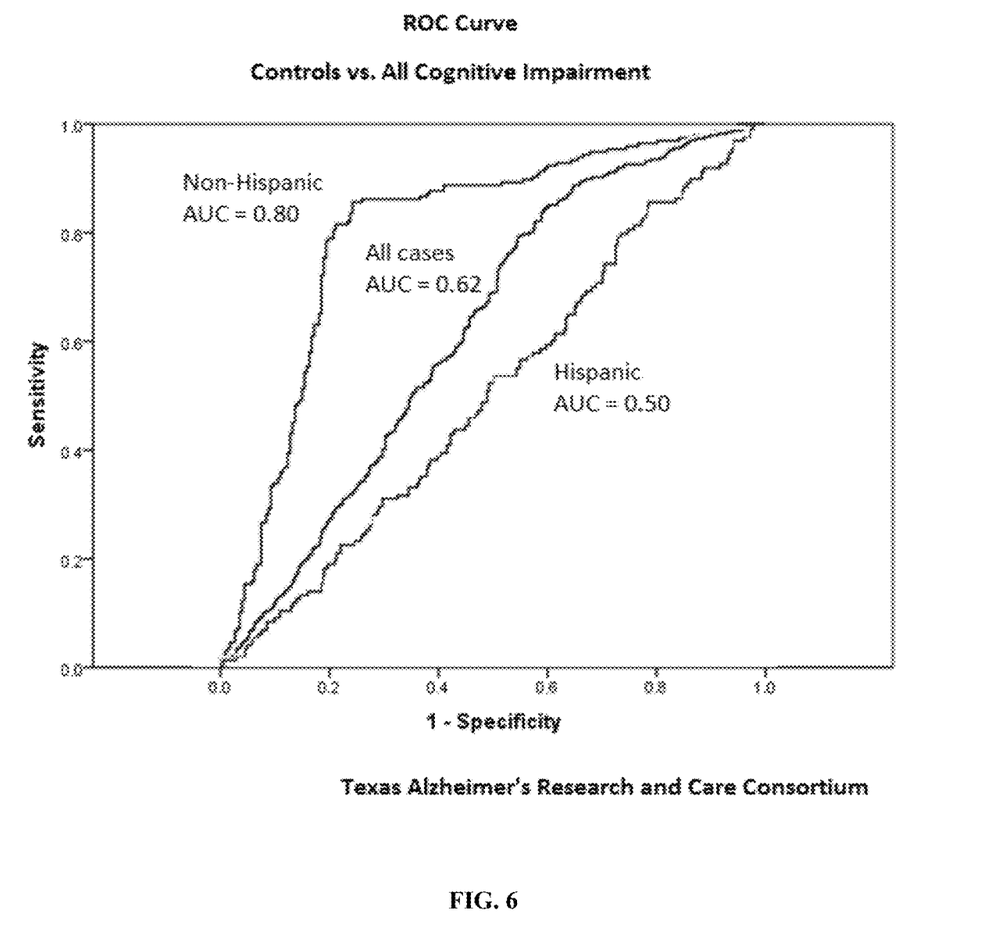
FIG. 6. ROC curves Controls vs. All Cognitive Impairment.

This suggests that this set of d's serum biomarkers is relevant to NHW, which is confirmed by ROC analyses. A latent variable indicated by 8 of the 11 biomarkers, adjusted for age, gender, education, apoe e4 status, and batch effects, accurately predicts observed clinical diagnoses (FIG. 4). The most accurate classification is found for control v. MCI in NHW (AUC=0.85) (FIG. 4).

Thus, the inventors have four major findings: (A) d scores are associated with 11 serum biomarkers. Only six of them have been previously associated with clinical dementia in TARCC by traditional methods (O'Bryant et al., 2010; 2011a, 2011b). None were identified in previous efforts in other cohorts (Ray et al., 2007; Gómez Ravetti et al., 2008). None have been previously associated with MCI; (B) The selected biomarkers suggest host innate immunological responses to microbiological infection may be responsible for dementia symptoms; (C) These biomarkers distinguish MCI from controls, i.e., they are altered in the earliest clinical stages of the disease and should make a useful diagnostic screening tool; and (D) They are less relevant to dementing illness in MA cases. Clinical "AD" in MA persons may be the result of a distinct biological mechanism.

The approach is modular, and can be easily adapted to other target conditions, potentially including, but not limited to, aging, depression, schizophrenia, or other difficult to assess conditions. The same advantages of latent variable vs. diagnostic based case-finding should apply to those disorders as well. Given the appropriate datasets, which are increasingly publically available, one should be able to construct accurate diagnostic blood tests for those disorders as well.

The TARCC baseline sample is relatively highly educated, and has a slight preponderance of females. The AD group is significantly older, less well educated, and more impaired relative to controls on multiple measures.

The inventors constructed a factor model of two latent variables: "g'" and "d". Together, these latent variables comprise "Spearman's g", i.e., a latent variable representing the shared variance across the observed cognitive performance variables. The model's design suggests that g' and d are orthogonal to each other. We confirmed that they are not significantly intercorrelated. Together, g' and d accounted for 59.6% of the variance in cognitive test performance. The latent construct d accounted for 37.2% independently of g'. The remainder was attributable to residual "measurement error". The observed cognitive measures all loaded significantly on d (range: r=0.50-0.73; all p≤0.001). It was also strongly and inversely associated with CDR-SB (r=−0.77). The latent variable g' was significantly indicated only by COWA (r=0.50) and DST (r=0.36) (both p≤0.001).

The latent variable d was strongly associated with caregiver rated IADL (partial r=−0.70, p<0.001, adjusted for age, gender, education, and ethnicity). By ROC, d's AUC for the discrimination of AD v. controls was 0.989. Its AUC for the discrimination of AD v. MCI was 0.938, and its AUC for the discrimination between controls and all other cases was 0.926. The latent variable d's AUC for the discrimination of MCI v. controls was 0.830. This improved over a previous model using IADL.

Multivariate regression models of serum biomarkers are predictors of d scores. Demographics explained 20% of d's variance. Significant independent predictors included age, education, and APOE e4 status. Neither gender nor ethnicity was significantly independently associated with d scores.

After adjusting for these covariates, INF-γ, IL-10 and IL-12p40 were each significantly associated with d scores. IL-13 showed a trend. These effects were weak, and explained an additional 13% of d's variance above and beyond the covariates.

Independent of both covariates and INF-γ, several of the AD biomarkers previously identified by O'Bryant et al. (2011) in TARCC were also associated with d scores. However, most were not. Only Thrombopoetin, von-Willebrand factor, and Stem Cell Factor were independently associated with d scores. These three biomarkers added an additional 5% of variance to the model. Together, INF-γ, serum biomarkers, apoe e4 and covariates explained 40% of variance in d scores.

A discriminate model of d score alone was significantly associated with TARCC adjudicated clinical diagnoses (77.4% correctly classified; Wilke's lambda=0.32; F (2, 1250)=1305.90, 9 p≤0.001). If demographics were added, this improved to 84.35% {=0.21; F (8, 1664)=251.78, p≤0.001}. If additionally IFN-γ and the batch effect were added, this increased to 87.73% [=0.25; F (12, 946)=77.46, p≤50.001]. When next Thrombopoetin, von-willebrand Factor, and Strem Cell Factor were added, only Throbopoeitin contributed significantly, IFN-γ and batch lost significance, and 89.61% were correctly classified [=0.23; F(18, 940)=57.70, p≤0.001] (Table 7). If finally, d was withdrawn, all variables regain significance, but only 73.00% of subjects are correctly classified [=0.23; F (18, 940)=57.70, p≤0.001]. This suggests that the associations between these biomarkers and TARCC adjudicated dementia status are mediated through their effect on d.

B. Methods

Subjects:

These data represent baseline data from the Texas Alzheimer's Research Consortium (TARCC) cohort (circa 2008-2009). Subjects included N=2016 TARCC participants [920 cases of Alzheimer's disease (AD), 277 "Mild Cognitive Impairment" (MCI) cases, and 819 controls]. The methodology of the TARCC project has been described in detail elsewhere [5]. Each participant underwent a standardized annual examination at the respective site that included a medical evaluation, neuropsychological testing, and clinical interview. Diagnosis of AD status was based on National Institute for Neurological Communicative Disorders and Stroke-Alzheimer's Disease and Related Disorders Association (NINCDS-ADRDA) criteria [6]. Controls performed within normal limits on their psychometric assessments. Institutional Review Board approval was obtained at each site and written informed consent was obtained for all participants.

Clinical Variables:

Instrumental Activities of Daily Living (ADL) were assessed using care-giver ratings. The ability to use the telephone, shopping, food preparation, housekeeping, laundry, use of transportation, ability to handle finances, and responsibility for medication adherence were each rated on the Likeart scale ranging from 0 (no impairment) to 3 (specific incapacity).

Cognitive Battery:

Executive control function measures: The Controlled Oral Word Association (COWA) is a test oral word production (verbal fluency). The patient is asked to say as many words as they can, beginning with a certain letter of the alphabet. Reduced word fluency scores are associated with frontal lobe impairment, particularly in the left hemisphere.

Memory:

Logical Memory II: Digit span sums the longest set of numbers the subject can repeat back in correct order (forwards and backwards) immediately after presentation on 50% of trails.

Verbal:

The Boston Naming Test (BOSTON [12]): This is a confrontation naming test that requires the subject to verbally name each of 60 line drawings of objects increasingly low frequency.

Non-Verbal:

WMS Visual Reproduction II [11]: The subject is asked to reproduce five, simple to complex figures following a thirty minute delay.

Outcome Measures:

The Clinical Dementia Rating Scale sum of boxes (CDR-SB) [13]: The CDR is used to evaluate dementia severity. The rating assesses the patient's cognitive ability to function in six domains—memory, orientation, judgment and problem solving, community affairs, home and hobbies and personal care. Information is collected during an interview with the caregiver. Optimal CDR-SB ranges corresponding to global CDR scores are 0.5-4.0, for a global score of 0.5, 4.5-9.0, for a global score of 1.0, 9.5-15.5, for a global score of 2.0, and 16.0-18.0, for a global score of 3.0[14].

The MMSE is a well known and widely used test for screening cognitive impairment. Scores range from 0 to 30. Scores less than 24 reflect cognitive impairment.

The Geriatric Dementia Rating Scale (GDS):

Depressive symptoms were assessed using the short Geriatric Depression Scale (GDS) [17, 18]. GDS scores range from zero-30. Higher scores are worse. A cut-point of 9-10 best discriminates clinically depressed from non-depressed elderly.

Statistical Analyses:

This analysis was performed using Analysis of Moment Structures (AMOS) software. Latent variables of interest were constructed from confirmatory factor analyses performed in a structural equation framework. Residual co variances were explicitly estimated for each observed measure. All observed measures, latent indicators and outcomes, were adjusted for age, gender and education. The latent variables of interest were validated as predictors of observed TARCC outcomes in multivariate regression models and by Receiver Operating Characteristic (ROC) analyses. Three multivariate regression models were developed using the latent variables as simultaneous predictors of SOB, MMSE and GDS scores. In ROC analyses, latent variables were used to predict TARCC adjusted dementia status (AD case vs. control), or CDR score>1.0.

Batch Effects:

TARCC's serum bio-markers exhibit a significant batch effort. Subject characteristics, i.e., age, gender, education, ethnicity, and APOE e4 status explain most (65%), but not all the variance in batch-related differences. Therefore, we decided to adjust all serum bio-marker values for demographic covariate adjusted batch effect. In order to achieve this, we ran our multivariate regression models in a SEM framework, using AMOS. The residuals were empirically adjusted to achieve good fit. All serum biomarkers were age, gender, education, ethnicity, and APOE e4 status, as well as for the residual of the batch value after its adjustment for the same variables.

Missing Data:

Some variables (e.g., VRII) were not used at all sites in TARCC's first wave. However, only the ROC analyses were limited to complete cases. Elsewhere, we used Full information Maximum Likelihood (FIML) methods to address missing data. FIML uses the entire observed data matrix to estimate parameters with missing data. In contrast to list wise or pair wise deletion, FIML yields unbiased parameter estimates, preserves the overall power of the analysis, and is arguably superior to alternative methods, e.g., multiple imputation.

Fit Indices:

The validity of structural models was assessed using two common test statistics. A non-significant chi-square signifies that the data are consistent with the model. The comparative fit index (CFI), with values ranging from between 0 and 1, compares the specified model with a model of no change. CFI values below 0.95 suggest model misspecification. Values of 0.95 or greater indicate adequate to excellent fit. A root mean square error of approximation (RMSEA) of 0.05 or less indicates a close fit to the data, with models below 0.05 considered "good" fit, and up to 0.08 as "acceptable". All three fit statistics should be simultaneously considered to assess the adequacy of the models to the data.

Roc Curves:

The diagnostic performance or accuracy of a test to discriminate diseased from normal cases can be evaluated using ROC curve analysis. Briefly the true positive rate (Sensitivity) is plotted as a function of the false positive rate (100-Specificity) for different cut-off points of a parameter. Each point of the ROC curve represents a sensitivity/specificity pairing corresponding to a particular decision threshold. The area under the ROC curve (AUC) is a measure of how well a parameter can distinguish between two diagnostic groups (diseased/normal). The analysis was performed in Statistical Package for the Social Sciences (SPSS).

REFERENCES

Arbuckle J L (2006) Analysis of Moment Structures-AMOS (Version 7.0) [Computer Program]. Chicago: SPSS.

Baldo et al. (2001) Verbal and design fluency in patients with frontal lobe lesions. *J Int Neurosci* 7, 586-596.

Barberger-Gateau et al. (1992) Instrumental activities of daily living as a screening tool for cognitive impairment and dementia in elderly community dwellers. *J Am Geriatr Soc* 40, 1129-1134.

Bennett et al. (2006) Cognitive, extrapyramidal, and mild cognitive impairment predictors of functional impairment in non-demented older community dwellers: The Sydney Older Person Study. *J Am Geriatr Soc* 54, 3-10.

Bentler (1990) Comparative fit indexes in structural models. *Psychol Bull* 107, 238-246.

Benton and Hamsher (1989) Multilingual Aphasia Examination. Iowa City, Iowa: AJA Associates.

Bollen and Long (1993) Testing Structural Equation Models. Sage Publications, Thousand Oaks, Calif.

Bouchard (2009) Genetic influence on human intelligence (Spearman's g): how much? *Ann Hum Biol* 36, 527-544.

Browne and Cudeck (1993) Alternative ways of assessing model fit, in Bollen, K. A., Long, J. S. (Eds.), Testing structural equation models Sage Publications, Thousand Oaks, Calif., pp. 136-162.

Buckner et al., (2005) Molecular, structural, and functional characterization of Alzheimer's disease: evidence for a relationship between default activity, amyloid, and memory. *J. Neurosci.* 25, 7709-7717.

Burton et al. (2009) Functional abilities in older adults with mild cognitive impairment. *Gerontol* 55, 570-581.

Byrne Structural Equation Modeling with AMOS—Basic Concepts, Applications, and Programming. LEA, 2001.

Cairns et al.; Consortium for Frontotemporal Lobar Degeneration. Neuropathologic diagnostic and nosologic criteria for frontotemporal lobar degeneration: consensus of the Consortium for Frontotemporal Lobar Degeneration. Acta Neuropathol. 2007; 114:5-22.

Chapman et al. Diagnosis of Alzheimer's disease using neuropsychological testing improved by multivariate analyses. J Clin Exp Neuropsychol. 2010; 32:793-808.

Choi et al. (2008) Multiple Bases of Human Intelligence Revealed by Cortical Thickness and Neural Activation. *J Neuroscience* 28, 10323-10329.

Chui et al. (1992) Criteria for the diagnosis of ischemic vascular dementia proposed by the State of California Alzheimer's Disease Diagnostic and Treatment Centers. *Neurol* 42, 473-480.

Committee on the Review of Omics-Based Tests for Predicting Patient Outcomes in Clinical Trials; Board on Health Care Services; Board on Health Sciences Policy; *Evolution of Translational Omics: Lessons Learned and the Path Forward.* Christine M. Micheel, Sharly J. Nass, and Gilbert S. Omenn, Editors; Institute of Medicine, Press of the National Academies, Washington, D.C., 2012.

Dowling et al. Latent structure and factorial invariance of a neuropsychological test battery for the study of preclinical Alzheimer's disease. Neuropsychology 2010; 24:742-756.

Duncan et al. (2000) A neural basis for general intelligence. *Science* 289, 457-460.

Duncan et al. (1997) Frontal lobe deficits after head injury: unity and diversity of function. *Cogn Neuropsychol* 14, 713-741.

Duncan and Owen (2000) Common regions of the human frontal lobe recruited by diverse cognitive demands. *Trends Neurosci.* 23, 475-483.

Folstein et al. (1975) Mini-mental state: a practical method for grading the cognitive state of patients for the clinician. *J Psychiatr Res* 12, 198-198.

Gläscher et al. (2010) Distributed neural system for general intelligence revealed by lesion mapping. *PNAS* 107, 4705-4709.

Goldberg et al. (2010) Performance-based measures of everyday function in mild cognitive impairment. *Am J Psychiatry* 167, 845-853.

Gōmez Ravetti M, Moscato P. Identification of a 5-protein biomarker molecular signature for predicting Alzheimer's disease. PLoS One. 2008; 3:e3111.

Gottfredson L S (1997) Why g matters: The complexity of everyday life. *Intelligence* 24, 79-132.

Grabowski and Damasio (1997) Definition, clinical features and neuroanatomica basis of dementia. In The Neuropathology of Dementia, Eisiri M M, Morris J H (eds). Cambridge University Press: Cambridge.

Graham (2009) Missing Data Analysis: Making it work in the real world. An *Rev Psychol* 6, 549-576.

Grundman et al. (2004) Alzheimer's Disease Cooperative Study. Mild cognitive impairment can be distinguished from Alzheimer disease and normal aging for clinical trials. *Arch Neurol* 61:59-66.

Hughes et al. (1982) A new clinical scale for the staging of dementia. *Br J Psychiatry* 140, 566-572.

Iavarone et al. (2007) Role of functional performance in diagnosis of dementia in elderly people with low educational level living in Southern Italy. *Aging Clin Exp Res* 19, 104-109.

Jefferson et al. (2008) Characterization of activities of daily living in individuals with mild cognitive impairment. *Am J Geriatr Psychiatry* 16, 375-383.

Kaplan et al. (1983) The Boston Naming Test. Experimental edition. Boston: Kaplan & Goodglass. 2nd ed., Philadelphia: Lea & Febiger.

Lawton and Brody (1969) Assessment of older people: self-maintaining and instrumental activities of daily living. *Gerontologist* 9, 179-186.

Loewenstein et al. An evaluation of the NINCDS-ADRDA neuropsychological criteria for the assessment of Alzheimer's disease: a confirmatory factor analysis of single versus multi-factor models. J Clin Exp Neuropsychol. 2001; 23:274-284.

Luck et al. (2011) Impact of impairment in instrumental activities of daily living and mild cognitive impairment on time to incident dementia: results of the Leipzig Longitudinal Study of the Aged. *Psychol Med* 41, 1087-1097.

McKeith et al. Report of the second dementia with Lewy body international workshop: diagnosis and treatment. Consortium on Dementia with Lewy Bodies. Neurology. 1999; 53:902-905.

McKhann et al. (1984) Clinical diagnosis of Alzheimer's disease: Report of the NINCDS-ADRDA Work Group. *Neurology* 34, 939-944.

Metz (1978) Basic principles of ROC analysis. Sem Nuc Med 8, 283-298.

O'Bryant et al. (2008) Texas Alzheimer's Research Consortium. Staging dementia using Clinical Dementia Rating Scale Sum of Boxes scores: a Texas Alzheimer's research consortium study. *Arch Neurol* 65, 1091-1095.

O'Bryant et al. Texas Alzheimer's Research & Care Consortium; Alzheimer's Disease Neuroimaging Initiative. A blood-based screening tool for Alzheimer's disease that spans serum and plasma: findings from TARC and ADNI. PLoS One. 2011b; 6:e28092.

O'Bryant et al. Texas Alzheimer's Research Consortium. A serum protein-based algorithm for the detection of Alzheimer disease. Arch Neurol. 2010; 67:1077-1081.

O'Bryant et al. Texas Alzheimer's Research and Care Consortium. A blood-based algorithm for the detection of Alzheimer's disease. Dement Geriatr Cogn Disord. 2011a; 32:55-62.

Palmer et al. Construct validity in health behavior research: Interpreting latent variable models involving self-report and objective measures. Journal of Behavioral Medicine. 2002; 25:525-550.

PASW Statistics 18, Release Version 18.0.0 (SPSS, Inc., 2009, Chicago, Ill., www.spss.com).

Pérès et al. (2006) Restriction in complex activities of daily living in MCI: impact on outcome. *Neurology* 67, 461-466.

Perneczky et al. (2006) Complex activities of daily living in mild cognitive impairment: conceptual and diagnostic issues. *Age Ageing* 35, 240-245.

Ray et al. Classification and prediction of clinical Alzheimer's diagnosis based on plasma signaling proteins. Nat Med. 2007; 13:1359-1362.

Román et al. Vascular dementia: diagnostic criteria for research studies. Report of the NINDS-AIREN International Workshop. Neurology. 1993; 43:250-260.

Royall (2006) Mild Cognitive Impairment and functional status. *J Am Geriatr Soc* 54:163-165.

Royall et al. and the Committee on Research of the American Neuropsychiatric Association (2002) Executive Control Function: A review of its promise and challenges to clinical research. *J Neuropsychiatry Clin Neurosci* 14, 377-405.

Royall et al. (2007) The cognitive correlates of functional status: A review from the Committee on Research of the American Neuropsychiatric Association. *J Neuropsychiatry Clin Neurosci* 19, 249-265.

Royall et al. The cognitive correlates of functional status: A review from the Committee on Research of the American Neuropsychiatric Association. Journal of Neuropsychiatry and Clinical Neurosciences, 2007; 19:249-265.

Royall et al. Pathological determinants of clinical dementia in Alzheimer's disease. Experimental Aging Research 2002; 28:143-162.

Royall et al. Validation of a latent variable representing the dementing process. Journal of Alzheimer's Disease, in press.

Royall et al. The Default Mode Network and Related Right Hemisphere Structures may be the Key Substrates of Dementia. Unpublished manuscript in review.

Royall and Palmer Advantages of a latent variable for dementia case-finding. Unpublished manuscript.

Royall and Palmer Getting Past "g": Testing a new model of dementing processes in non-demented persons. Journal of Neuropsychiatry and Clinical Neurosciences, 2012; 24:37-46.

Ruscio and Ruscio (2002) A structure-based approach to psychological assessment: matching measurement models to latent structure. *Assessment* 9:4-16.

Salthouse (2005) Relations between cognitive abilities and measures of executive functioning. *Neuropsychol* 19, 532-545.

Schafer and Graham (2002) Missing data: Our view of the state of the art. *Psychol Methods,* 7, 147-177.

Sheikh and Yesavage (1986) Geriatric Depression Scale (GDS): Recent evidence and development of a shorter version. *Clin Gerontologist* 5, 165-173.

Spearman (1904) General intelligence, objectively determined and measured. *Am J Psychol* 15:201-293.

Spearman and Wynn Jones, Human Ability. Macmillan & Co. London, 1951.

Stuss et al. (1998) The effects of focal anterior and posterior brain lesions on verbal fluency. *J Int Neurosci* 4, 265-278.

Tombaugh and McIntyre (1992) The mini-mental state examination: A comprehensive review. *J Am Geriatrics Soc* 40, 922-935.

Waring et al. for the Texas Alzheimer's Research Consortium (2008) The Texas Alzheimer's Research Consortium longitudinal research cohort: Study design and baseline characteristics. *Texas Pub Health J* 60, 9-13.

Wechsler (1997) Wechsler Memory Scale—Third Edition. San Antonio, Tex.: The Psychological Corporation.

Winblad et al. (2004) Mild cognitive impairment. Beyond controversies, towards a consensus: Report of the International Working Group on Mild Cognitive Impairment. *J Intern Med* 256:240-246.

Zweig and Campbell (1993) Receiver-operating characteristic (ROC) plots: a fundamental evaluation tool in clinical medicine. *Clin Chem* 39, 561-577.

The invention claimed is:

1. A method for treating mild cognitive impairment (MCI) in a non-hispanic subject comprising,
   (a) obtaining a blood sample from a non-hispanic subject;
   (b) contacting the biological sample with reagents that specifically bind and form a complex with IL-13 and alpha 2 macroglobulin biomarkers forming a reagent biomarker complex;
   (c) detecting the reagent biomarker complex of IL-13 and alpha 2 macroglobulin and determining the level of the biomarkers in the sample; and
   (d) administering treatment for MCI to the subject when the level of the biomarkers in the sample is increased with respect to a control level.

* * * * *